US010238420B2

(12) United States Patent
Karve et al.

(10) Patent No.: US 10,238,420 B2
(45) Date of Patent: Mar. 26, 2019

(54) NON-REUSABLE INTRA-OSSEOUS ACCESS DEVICE AND METHOD THEREOF

(71) Applicant: SECRETARY, DEPARTMENT OF BIOTECHNOLOGY, New Delhi (IN)

(72) Inventors: Jayant Sitaram Karve, Maharashtra (IN); Sandeep Singh, Delhi (IN)

(73) Assignee: SECRETARY, DEPARTMENT OF BIOTECHNOLOGY, New Delhi (IN)

( * ) Notice: Subject to any disclaimer, the term of this patent is extended or adjusted under 35 U.S.C. 154(b) by 134 days.

(21) Appl. No.: 15/311,578

(22) PCT Filed: Dec. 19, 2014

(86) PCT No.: PCT/IB2014/067140
§ 371 (c)(1),
(2) Date: Nov. 16, 2016

(87) PCT Pub. No.: WO2015/177612
PCT Pub. Date: Nov. 26, 2015

(65) Prior Publication Data
US 2017/0105763 A1   Apr. 20, 2017

(30) Foreign Application Priority Data
May 19, 2014 (IN) .......................... 1318/DEL/2014

(51) Int. Cl.
*A61B 17/34* (2006.01)
*A61B 10/02* (2006.01)
*A61M 5/158* (2006.01)
*A61B 17/00* (2006.01)
*A61B 90/00* (2016.01)

(52) U.S. Cl.
CPC ........ *A61B 17/3472* (2013.01); *A61B 10/025* (2013.01); *A61M 5/158* (2013.01); *A61B 2010/0258* (2013.01); *A61B 2017/0023* (2013.01); *A61B 2090/0814* (2016.02)

(58) Field of Classification Search
CPC .............. A61B 17/3472; A61B 10/025; A61B 2090/0814; A61B 2010/0258; A61B 2017/0023; A61M 5/158
See application file for complete search history.

(56) References Cited

U.S. PATENT DOCUMENTS 5,195,985 A   3/1993   Hall

FOREIGN PATENT DOCUMENTS

WO   2005/046769 A2   5/2005
WO   2011/070593 A1   6/2011

OTHER PUBLICATIONS

International Search Report and Written Opinion from corresponding International Patent Application No. PCT/IB2014/067140, dated Jun. 2, 2015, 8 pages.

*Primary Examiner* — Amber Stiles
(74) *Attorney, Agent, or Firm* — Merchant & Gould P.C.

(57) ABSTRACT

Disclosed is a non-reusable intra-osseous access device and method thereof. The non-reusable intra-osseous access device which can be easily rendered non-reusable after establishing the access into the marrow region includes the automatic locking of driver unit 5 after removal of needle and trocar assembly from the driver unit. Further, the non-reusable intra-osseous access device also includes the non-loading of the trocar and or needle hub and or trocar with needle hub.

19 Claims, 8 Drawing Sheets

8- Multi-splined shaft

Configuration-1

Configuration-2

Configuration-3

Detail-B
Needle end with multiple external cutting grooves.

NON-REUSABLE INTRA-OSSEOUS ACCESS DEVICE AND METHOD THEREOF

This application is a National Stage Application of International Patent Application No. PCT/IB2014/067140, filed 19 Dec. 2014, which claims benefit of Serial No. 1318/DEL/2014, filed 19 May 2014 in India and which applications are incorporated herein by reference. To the extent appropriate, a claim of priority is made to each of the above disclosed applications.

TECHNICAL FIELD

The present subject matter described herein, in general relates to apparatus and methods to accessing bone marrow at various target areas including, but not limited to, a patient's proximal tibia, and more particularly, to an intra-osseous access device and bone marrow aspiration device, which can get the access to the bone through hard cortical region, and which can be easily rendered non-reusable after establishing the access into the marrow region.

BACKGROUND

Rapid vascular access is critical in resuscitation of patients during clinical emergency. Even though peripheral intravenous (IV) access is a preferred, many a times it is difficult to access these veins. This usually happens in patients of cardiac arrest, trauma, profound blood loss, severe dehydration and burn injury especially in the pre-hospital setting. Failure rates of peripheral IV access in these emergency conditions have been reported in 10-40% cases. Precious time is lost to access these collapsed peripheral veins in this golden period of patient care. This delay leads to substantial morbidity and mortality.

Intraosseous (IO) access is an alternative to difficult IV access under these clinical situations. IO access allows infusion of fluids directly into the intra-medullary space of the long bones. This space, where the IO needle gets inserted is highly vascular and provides a direct conduit to the systemic circulation. These intra-medullary venous channels are supported by bony matrix, keeping it open even in the presence of shock.

Intra-osseous infusion has long been the standard of care in pediatric emergencies when rapid IV access is not possible. The U.S. military used the hand driven IO needles for infusions extensively and successfully during World War II. However, such IO needles were cumbersome, difficult to use, and often had to be manually driven into a bone.

Drugs administered intra-osseously enter a patient's blood circulation system as rapidly as they do when given intravenously. In essence, bone marrow may function as a large non-collapsible vein.

Traditionally, the bone marrow aspiration process may be conceded out by inserting the needle through the skin into the bone and a syringe is used to draw out the bone marrow. Conventional devices for achieving bone marrow aspiration include a needle with a trocar that is put in the bone either manually or through springs. The impact of the needle may result in bone fracture and pain to the patient. Further, in conventional devices, while accessing the bone marrow due to lack of controlled movement of the needle involves a risk of either needle overshoot or undershoot through cortical layers of the bone. This is mainly because of uncertainty or blindness associated with the procedure, as the operator is not aware of the position of the needle.

Further, in the conventional devices used for bone marrow aspiration, the needle bends or breaks due to the force applied particularly in adult patients who have hard, calcified cortical layer of bone. Also the operators tend to use the same needle for multiple aspirations, thereby leading to infections.

In resource constrained settings, it is important to have a device which is ready to use with no preparation required on-site. Also, such device once used, should not be re-usable to prevent infections. The available devices are reusable and need sterilization prior to use which is a great drawback in resource-constrained setting.

The process of sterilization prior to use is a time consuming process and many times even after the sterilization there is a risk of contamination and possibility of spreading infection by the re-use of the device.

With reference to the above mentioned drawbacks there is need for a non-reusable intra-osseous access device and bone marrow aspiration device, which can get the access to the bone through hard cortical region, and which can be easily rendered non-reusable after establishing the access into the marrow region.

SUMMARY

This summary is provided to introduce concepts related a non-reusable intra-osseous access device and method thereof. This summary is not intended to identify essential features of the subject matter nor is it intended for use in determining or limiting the scope of the subject matter.

In one implementation, a non-reusable intra-osseous access device which can be easily rendered non-reusable after establishing the access into the marrow region includes the automatic locking of driver unit after removal of needle and trocar assembly from the driver unit is disclosed.

In one implementation, non-reusable intra-osseous access device which can be easily rendered non-reusable after establishing the access into the marrow region includes the non-loading of the trocar and or needle hub and or trocar with needle hub is disclosed.

Accordingly in one implementation, a non-reusable intra-osseous access device is disclosed. The non-reusable intra-osseous access device comprises of a multi-splined axial shaft 8 engaged with the multi-spiral nut 5, assembly of trocar holder 10 and needle hub 11 engaged at one end of the multi-spiral axial shaft 8 and drive handle 1 coupled to the multi-spiral nut 5 through the inner barrel 2. A multi-spiral axial shaft 8 has a hollow axial cavity 8g and radial opening 8a on shaft surface 8.

In one implementation, a non-reusable Intraosseous (IO) device is disclosed. The device comprises of a handle capable of being displaced by applying force, the handle comprising a spring-clutch and an inner barrel; a multi-splined axial shaft engaged with the multi-spiral nut and is capable of being rotated, the multi-splined axial shaft comprising an axial hollow cavity and at least one opening; a needle hub comprising at least one needle; and when the handle is displaced axially down, it compresses the spring-clutch and engages with inner barrel, thereby enabling the multi-spiral nut to move axially down, and rotating the multi-splined shaft, thereafter transferring the rotational motion and axial thrust to the trocar holder and the needle hub, and enabling access through an injection site by rotational piercing action. The device further comprises of an automatic locking mechanism, operating after enabling access through the injection site, comprising: at least one expandable element, a trocar holder comprising a trocar and a trocar holder shaft, wherein the trocar holder is inside the multi-splined shaft with a trocar holder shaft inside the axial hollow cavity, and the expandable element is configured to protrudes outside the opening preventing axial up-down motion of the multi-spiral nut along the multi-splined shaft rendering the non-reusable Intraosseous (IO) device non-reusable.

In one implementation, a non-reusable Intraosseous (IO) device is disclosed. The device comprises of the automatic locking mechanism, operating after enabling access through the injection site, wherein the trocar holder and needle hub are configured to be dismantled thereby leading to prevention of the rotation of the multi-splined shaft and making the device non-reusable, by breaking the tearable pouch causing the liquid adhesive within the tear-able pouch to ooze out of the opening, wherein one end of the tear-able pouch is attached to one end of the trocar holder shaft.

In one implementation, a non-reusable Intraosseous (10) device is disclosed. the device comprises of a handle capable of being displaced by applying force, the handle comprising a spring-clutch and an inner barrel; a multi-splined axial shaft capable of being rotated, the multi-splined axial shaft comprising a tear able pouch filled with adhesive material in a axial hollow cavity and at least one opening; a locking mechanism comprising at least one expandable element, a trocar holder comprising a trocar and a trocar holder shaft; and a needle hub comprising at least one needle. The trocar holder is inside the multi-splined shaft with a trocar holder shaft inside the axial hollow cavity to block the opening, preventing the expandable element to protrude outside the multi-splined shaft through opening; and when the handle is displaced axially down, it compresses the spring-clutch and engages with inner barrel, thereby enabling the multi-spiral nut to move axially down, and rotating the multi-splined shaft, thereafter transferring the rotational motion and axial thrust to the trocar holder and the needle hub, and enabling access through an injection site by rotational piercing action.

In one implementation, a method for using a non-reusable Intraosseous device having a handle capable of being displaced by applying force, the handle comprising a spring-clutch and an inner barrel; multi-splined axial shaft capable of being rotated, the multi-splined axial shaft comprising a tear able pouch filled with adhesive material in a axial hollow cavity and at least one opening; a locking mechanism comprising at least one expandable element, a trocar holder comprising a trocar and a trocar holder shaft; and a needle hub comprising at least one needle is disclosed. The method comprises of: targeting the non-reusable Intraosseous device on the injection site; placing the non-reusable Intraosseous device on the injection site; and applying pressure/force on the non-reusable Intraosseous device to insert the needle by rotational drilling into the injection site thereby establishing access into the injection site.

In one implementation, if the excess force is applied on the handle, it does not get transmitted to trocar and needle holder assembly due to slippage of the trocar holder and needle hub with reference to multi-splined shaft, preventing the damage to the piercing site.

Conventional needles used in accessing bone marrow at various target areas have a single point diamond tip used for piercing. In the present the non-reusable Intraosseous (IO) device, comprises a multiple (at least two) cutting edges along the periphery with flutes of the drilling tip for smooth removal of the hard cortical layer by shearing of hard cortical layer radially. This ensures smooth insertion through the bone as compared to axial piercing action or insertion by diamond tip with rotation allowing bone chips if any to be displaced out radially.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The detailed description is described with reference to the accompanying figures. In the figures, the left-most digit(s) of a reference number identifies the figure in which the reference number first appears. The same numbers are used throughout the drawings to refer like features and components.

Figure 15:
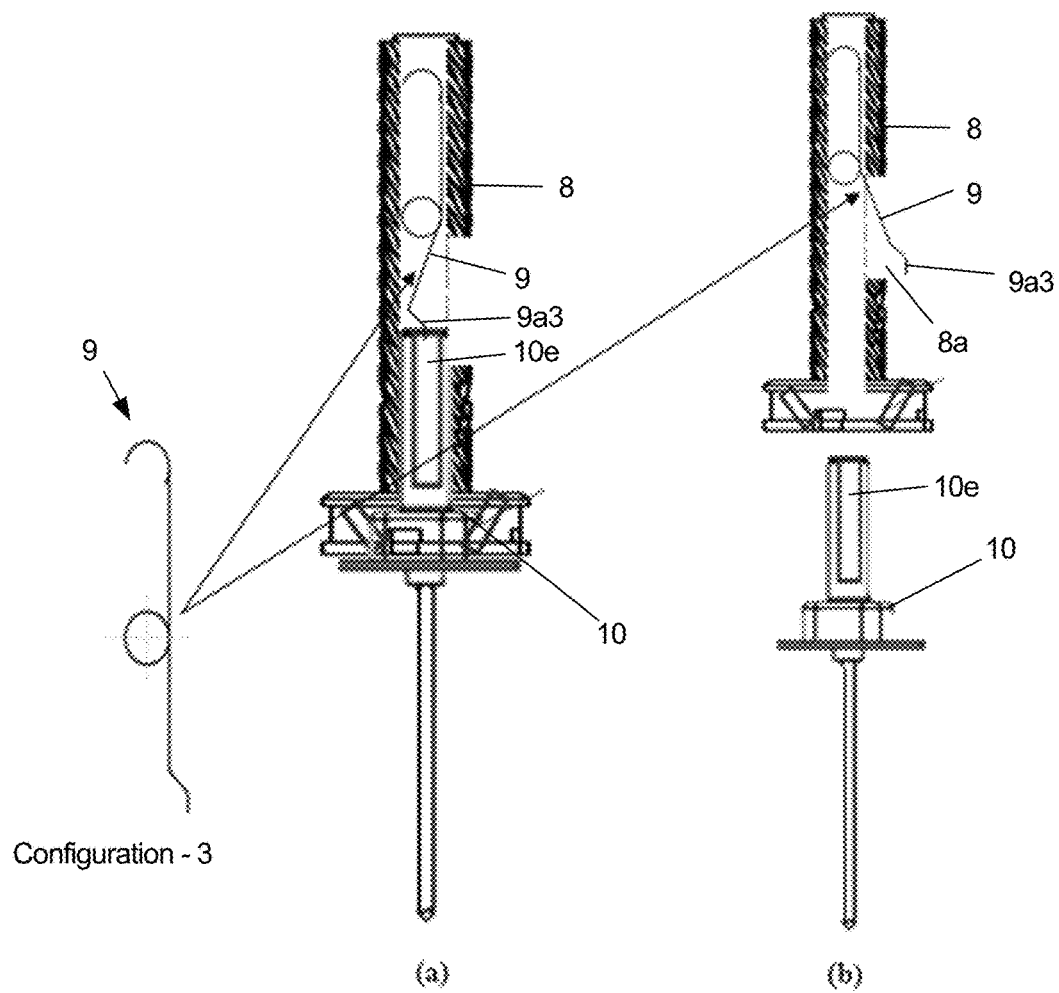

FIGS. 15(a) and (b) illustrates a locking element 9, positioned inside the multi splined shaft 8 and a locking element 9, positioned removed from the multi splined shaft 8, in accordance with an embodiment of the present subject matter.

DETAILED DESCRIPTION OF THE PRESENT INVENTION

Preferred embodiments of the present disclosure will be described herein below with reference to the accompanying drawings. In the following description, well-known functions or constructions are not described in detail to avoid obscuring the present disclosure in unnecessary detail.

The terms and words used in the following description are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention.

It is to be understood that the singular forms "a," "an," and "the" include plural referents unless the context clearly dictates otherwise.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The various components are used in the present invention; the components with the numbering mentioned in the accompanying figures are listed below:

| | | |
|---|---|---|
| 1. Handle | 2. Inner barrel | 3. Spring-clutch |
| | 2a-Clutch surface | |
| | 2b-spring seating | |
| 4. Spring-lead screw | 5. Multi-spiral nut | 6. Protection cover |
| 7. Spring seating Cap | 8. Multi-splined shaft | 9. Locking cylinder |
| | 8a-Opening | 9b1-locking holder |
| | 8b-seating for trocar + needle assembly | 9a1-expandable element |
| | | 9a2-expandable element |
| | 8c-seating | 9b2-locking holder |
| | 8d multi spline | 9c2-spring |
| | 8e-Stiff protrusion | 9a3-expandable element |
| | 8f-tear able pouch filled with adhesive material | 9b3-Spring eyelet |
| | | 9c3-Locking arm with bend end |
| | 8g-axial hollow cavity | |
| 10. Trocar Holder | 11. Needle Hub | 12. Other Parts |
| 10a-trocar | 11a-Needle | 12a-cylindrical wrap |
| 10/10b-trocar holder | 11/11b-Needle Hub | 12b-engaging protrusion |
| 10c-hollow cavity | 11b1-locking surface/grove | 12c-tear grip |
| 10d-locking surface | 11c-Hub inlet | |
| 10e-trocar holder shaft | | |

In one implementation, a non-reusable intra-osseous access device is disclosed. The intra-osseous access device comprises of a multi-splined axial shaft 8 engaged with the multi-spiral nut 5, assembly of trocar holder 10 and needle hub 11/11b engaged at one end of the multi-spiral axial shaft 8 and drive handle 1 coupled to the multi-spiral nut 5 through the inner barrel 2. A multi-spiral axial shaft 8 has a hollow axial cavity 8g and radial opening 8a on shaft surface 8.

The handle 1 and inner barrel 2 are coupled with spring and clutch surfaces. When the handle 1 is pressed down, it compresses the spring clutch 3 and engages with inner barrel 2. When handle 1 is pressed down, the multi-spiral nut 5 moves axially down, this rotates the multi-splined shaft 8. The multi-splined shaft may be covered using a protection cover 6 which is further engaged with the handle 1 at one end and the assembly of trocar holder 10 at other end.

The spring 4, between spring seating cap 7 and inner barrel 2 gets compressed during downward motion of the handle 1 and released during upward motion of the handle 1.

Trocar holder 10 and needle hub 11b are engaged at distal end of multi-spiral shaft 8. The assembly of trocar holder 10 and needle hub 11b may be engaged with multi-splined shaft through locking cylinder 12. The rotational motion and axial thrust of the multi-spiral shaft 8 is transferred to the Trocar holder 10 and needle hub for gaining the access through hard cortical layer of the bone by rotational piercing action.

In one implementation, the locking element 9 seats inside the multi-splined shaft 8. The locking element has expandable element 9a1. In assembled condition, expandable element 9a1 is locked inside the hollow cavity 10c of trocar holder 10. The trocar holder 10 is seating inside the multi-splined shaft 8 with trocar holder shaft 10e inside the axial hollow cavity 8g such that the opening 8a is blocked, preventing expandable element 9a1 to protrude outside the multi-splined shaft 8 through opening 8a.

Post insertion of the hard cortical layer of the bone by the device, the trocar holder 10 and needle hub 11b are dismantled from the rest of the device. This leads to unlocking of the expandable element 9a1 from the hollow cavity 10c. The expandable element 9a1 protrudes outside the opening 8a preventing axial up-down motion of the multi-spiral nut 5 along the multi-splined shaft 8. This leads to prevention of rotation of the multi-splined shaft 8 rendering the device non-reusable post insertion and dismantling of the trocar holder 10 and needle hub 11b from the rest of the device.

In one implementation, the locking element 9 seats inside the multi-splined shaft 8. The locking element has expandable element 9a2. In assembled condition, expandable element 9a1 is locked inside the hollow cavity 10c of trocar holder 10. The trocar holder 10 is seating inside the multi-splined shaft 8 with trocar holder shaft 10e inside the axial hollow cavity 8g such that the opening 8a is blocked, preventing expandable element 9a2 to protrude outside the multi-splined shaft 8 through opening 8a.

Post insertion of the hard cortical layer of the bone by the device, the trocar holder 10 and needle hub 11b are dismantled from the rest of the device. This leads to unlocking of the expandable element 9a2 from the hollow cavity 10c. The spring 9c2 presses the expandable element 9a2 which leads to the expandable element 9a2 protrude outside the opening 8a preventing axial up-down motion of the multi-spiral nut 5 along the multi-splined shaft 8. This leads to prevention of rotation of the multi-splined shaft 8 rendering the device non-reusable post insertion and dismantling of the trocar holder 10 and needle hub 11*b* from the rest of the device.

In one implementation, the locking element 9 seats inside the multi-splined shaft 8. The locking element has expandable element 9*a*3. In assembled condition, expandable element 9*a*3 is locked inside the hollow cavity 10*c* of trocar holder 10. The trocar holder 10 is seating inside the multi-splined shaft 8 with trocar holder shaft 10*e* inside the axial hollow cavity 8*g* such that the opening 8*a* is blocked, preventing expandable element 9*a*3 to protrude outside the multi-splined shaft 8 through opening 8*a*.

Post insertion of the hard cortical layer of the bone by the device, the trocar holder 10 and needle hub 11*b* are dismantled from the rest of the device. This leads to unlocking of the expandable element 9*a*3 from the hollow cavity 10*c*. The spring eyelet 9*b*3 presses the expandable element 9*a*3 which leads to the expandable element 9*a*3 protrude outside the opening 8*a* preventing axial up-down motion of the multi-spiral nut 5 along the multi-splined shaft 8. This leads to prevention of rotation of the multi-splined shaft 8 rendering the device non-reusable post insertion and dismantling of the trocar holder 10 and needle hub 11*b* from the rest of the device.

In one implementation, a tear-able pouch filled with liquid adhesive 8*f* is fixed within the hollow cavity 8*g* such that it is positioned close to the opening 8*a* and one end is adhering to the inner cavity 8*g* of multi-spline shaft 8. The other end of the tear-able pouch 8*f* is attached to the distal end of the trocar holder shaft 10*e*.

Post insertion of the hard cortical layer of the bone by the device, the trocar holder 10 and needle hub 11*b* are dismantled from the rest of the device. This leads to breaking of the tear-able pouch 8*f*. The liquid adhesive within the pouch oozes out of the opening 8*a*.

In one case, upon solidification of the adhesive on splined surface 8*d* prevents axial up-down motion of the multi-spiral nut 5 along the multi-splined shaft 8. This leads to prevention of rotation of the multi-splined shaft 8 rendering the device non-reusable post insertion and dismantling of the trocar holder 10 and needle hub 11*b* from the rest of the device.

In another case, the multi-spiral nut 5 gets adhered to multi-splined shaft 8 upon solidification of the adhesive on splined surface 8*d* prevents axial up-down motion of the multi-spiral nut 5 along the multi-splined shaft 8. This leads to prevention of rotation of the multi-splined shaft 8 rendering the device non-reusable post insertion and dismantling of the trocar holder 10 and needle hub 11*b* from the rest of the device.

In one implementation, the multi-splined shaft 8 is multi segmented with at least one independent segment (example 8*d*2 in between 8*d*1 and 8*d*3). The multiple segments are held together to form a single shaft 8 by the trocar holder shaft 10*e* during assembled condition of the device. Trocar holder shaft 10*e* had a section with at least one flat surface so that there is no relative rotation and axial movement of segments (example 8*d*1, 8*d*2 and 8*d*3). Hence in assembled condition, the multi-spiral nut 5 moves up-down along the multi-splined shaft 8, leads to transfer of rotational motion to of the trocar holder 10 and needle hub 11*b* during insertion.

Post insertion of the hard cortical layer of the bone by the device, the trocar holder 10 and needle hub 11 are dismantled from the rest of the device. This leads to removal of the trocar holder shaft 10*e* leading to disintegration of the multi-splined shaft 8 into its segments. This prevents any rotation of one of the segment (example 8*d*1, 8*d*2 and 8*d*3) to the trocar holder 10 and needle hub 11*b* for subsequent insertion.

Also, the multiple segments of the multi-splined shaft 8 prevents insertion of the trocar holder shaft 10*e* into the axial hollow cavity 8*g* rendering the 10 device non-reusable for subsequent insertion.

In one implementation, the multi-splined shaft 8 at one distal end has a stiff protrusions 8*e* which normally prevents the trocar holder 10 to be seated in assemble condition. The assembly between multi-splined shaft 8 and trocar holder 10 is pre-fitted.

Post insertion of the hard cortical layer of the bone by the device, the trocar holder 10 and needle hub 11*b* are dismantled from the rest of the device. This leads to the return of the stiff protrusions 8*e* to their original position shrinking the opening. This prevents re-insertion of the trocar holder 10 and needle hub 11*b* back into the device rendering the device non-reusable once it is used.

In one implementation, to facilitate the insertion through the rotational action of the trocar hub and needle holder assembly, the needle has external cutting edges along the spirals of external surface.

In one implementation, multi segment lead screw: e.g., 8*d*1, 8*d*2, 8*d*3, when trocar shaft is inserted inside, it becomes single unified shaft. Hence rotation due to nut movement is transferred to trocar with needle assembly. When the trocar is taken out of lead screw, it becomes three piece/multi piece. Hence the rotation induced due to up-down motion of lead screw is not imparted to the trocar needle assembly. This makes the device non-reusable.

Figure 10:
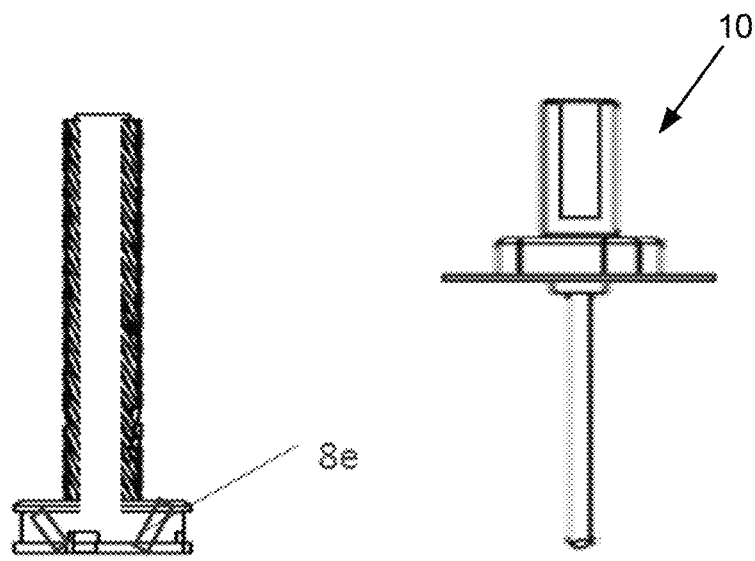
FIG. 10 illustrates a stiff protrusion: when trocar is not in place is shown, in accordance with an embodiment of the present subject matter.

In one implementation, (as shown in FIG. 10), the trocar with needle assembly is pre-fitted into this lead screw seating. When the trocar is removed from the lead screw, 8*e* protrude out making the inlet smaller and prevent trocar with needle to insert back. This makes the device non reusable.

In one implementation, when trocar shaft is pulled out, the pouch 8*f* breaks, the adhesive oozes out on the splined surfaces. The splined surface with adhesive prevent nut to move up and down. In another embodiment, the nut gets stuck with the splined shaft.

Figure 1:
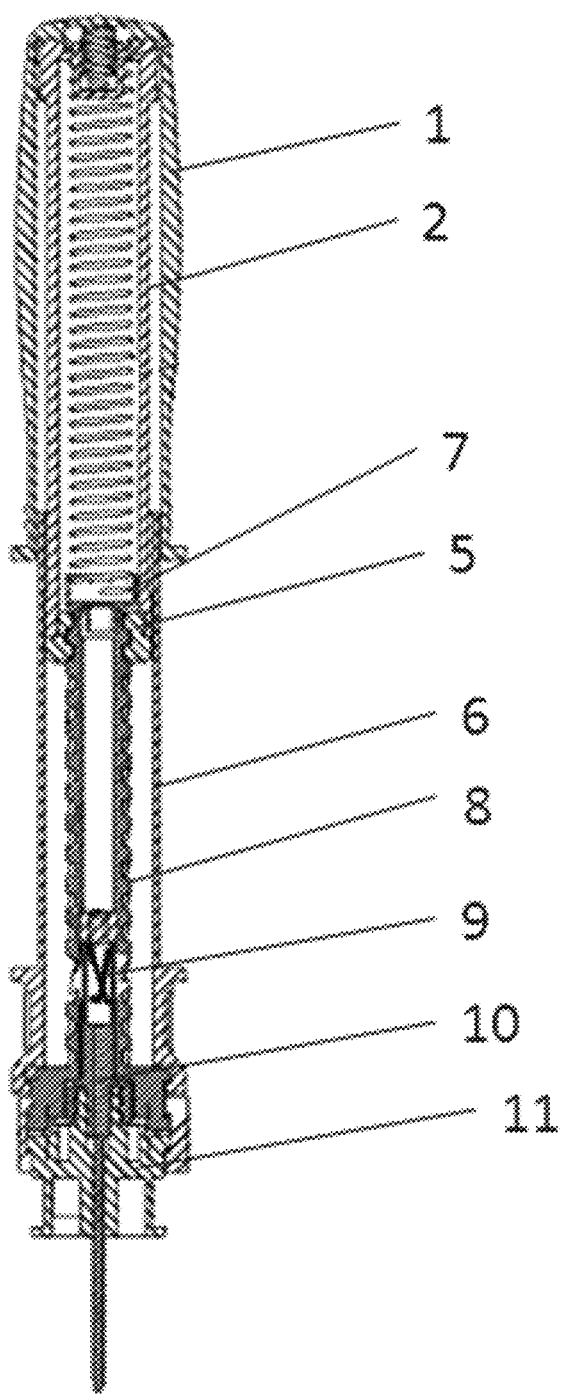
FIG. 1 illustrates a non-reusable IO device is shown, in accordance with an embodiment of the present subject matter.

Referring to FIG. 1 illustrates a non-reusable IO device, in accordance with an embodiment of the present subject matter.

Figure 2:
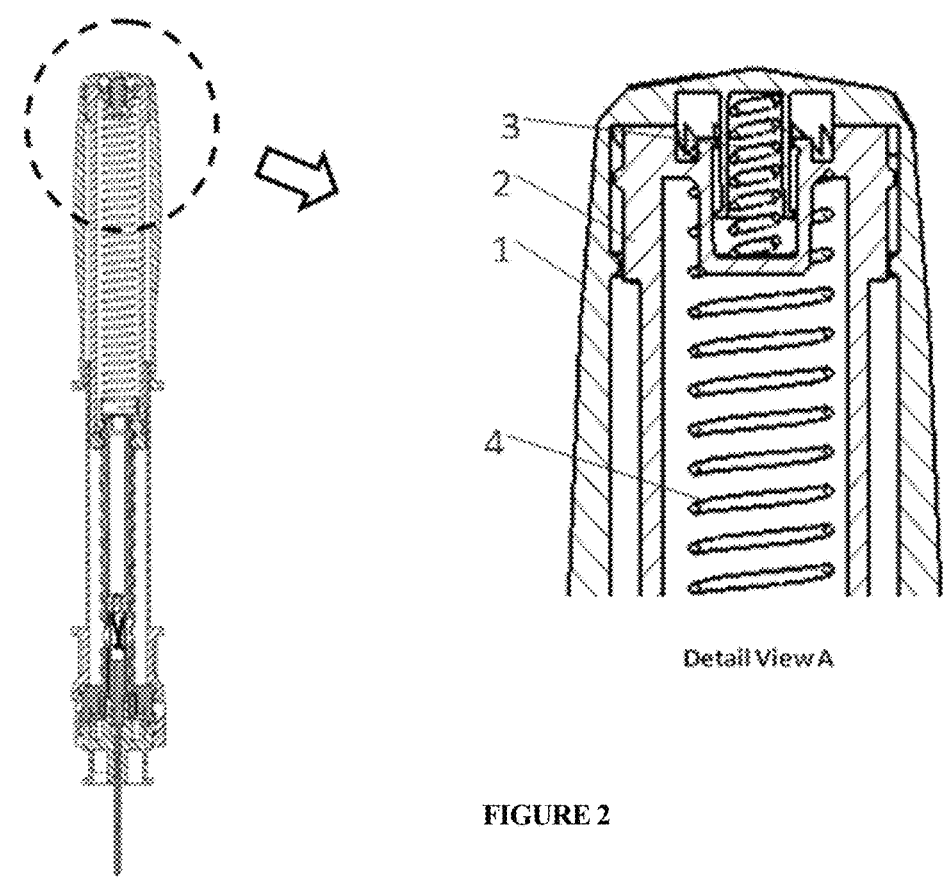
FIG. 2 illustrates a top portion comprising handle, inner barrel; spring-clutch and spring lead screw is shown, in accordance with an embodiment of the present subject matter.

Referring to FIG. 2 illustrates a top portion comprising handle, inner barrel; spring-clutch and spring lead screw, in accordance with an embodiment of the present subject matter.

Figure 3:
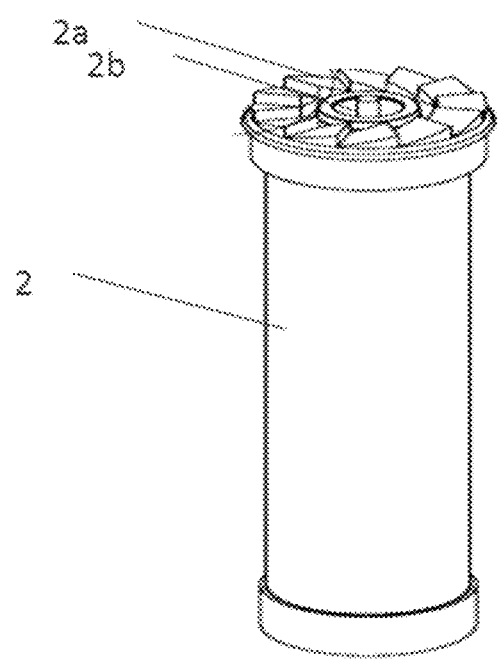
FIG. 3 illustrates an inner barrel is shown, in accordance with an embodiment of the present subject matter.

Referring to FIG. 3 illustrates a 2-inner barrel, in accordance with an embodiment of the present subject matter. In one implementation, as shown in FIG. 3, the inner barrel 2 comprises of a clutch surface 2*a* and a spring seating 2*b*. The operation of working of the inner barrel 2 in conjugation with the other components of the device is as explained above.

Figure 4:
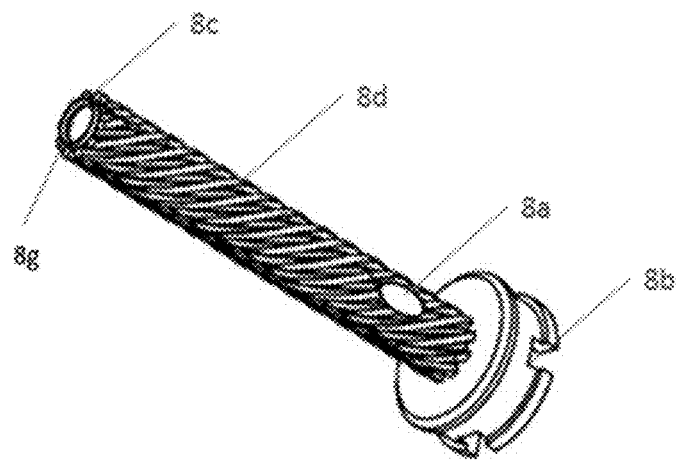
FIG. 4 illustrates multi-splined shaft is shown, in accordance with an embodiment of the present subject matter.

Referring to FIG. 4 illustrates multi-splined shaft 8, in accordance with an embodiment of the present subject matter. In one implementation, as shown in FIG. 4, the multi-splined shaft 8 comprises of the opening 8*a*, a seating for trocar+needle assembly 8*b*, a seating 8*c*, a multi spline 8*d*, the stiff protrusion 8*e*, the tear able pouch filled with adhesive material 8*f*, and the axial hollow cavity 8*g*. The operation of working of the multi-splined shaft 8 in conjugation with the other components of the device is as explained above.

Figure 5:
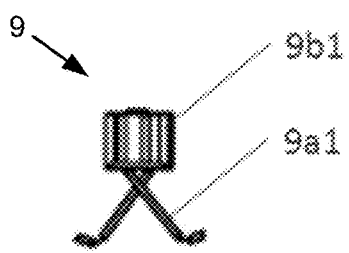
FIG. 5 illustrates a 9 locking Element Configuration-1, Configuration-2, and Configuration-3 is shown, in accordance with an embodiment of the present subject matter.
Figure 5:
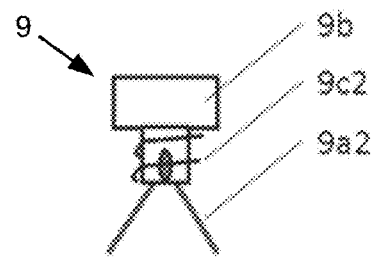
Figure 5:
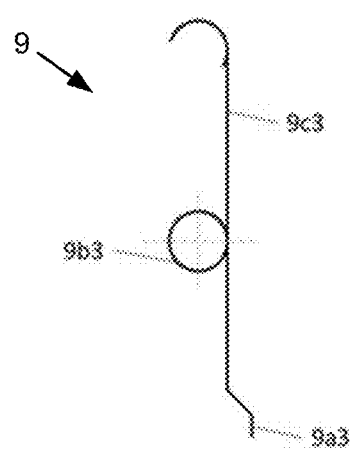

Referring to FIG. 5 illustrates a 9 locking Element Configuration-1, Configuration-2, and Configuration-3 in accordance with an embodiment of the present subject matter.

Figure 6:
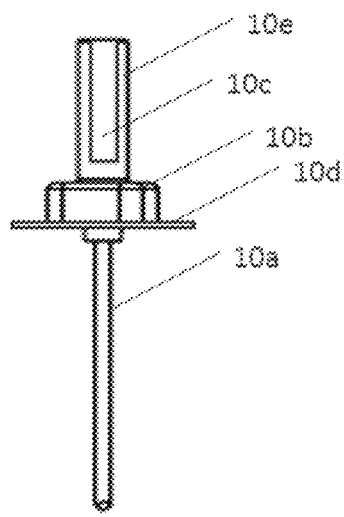
FIG. 6 illustrates a trocar holder is shown, in accordance with an embodiment of the present subject matter.

Referring to FIG. 6 illustrates a trocar holder, in accordance with an embodiment of the present subject matter. In one implementation, as shown in FIG. 6, the trocar holder 10/10b, comprises of the trocar 10a, a hollow cavity 10c, a locking surface 10d, and a trocar holder shaft 10e. The operation of working of the trocar holder 10/10b in conjugation with the other components of the device is as explained above.

Figure 7:
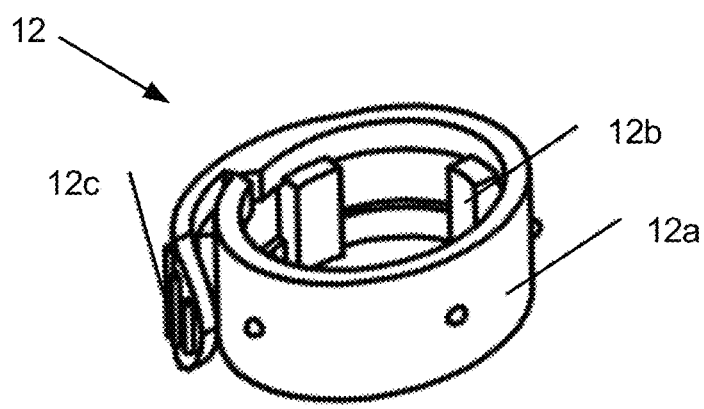
FIG. 7 illustrates other parts of the overall process is shown, in accordance with an embodiment of the present subject matter.

Referring to FIG. 7 illustrates other parts of the overall process, in accordance with an embodiment of the present subject matter. In one implementation, as shown in FIG. 7 the other parts 12 comprises a cylindrical wrap 12a, an engaging protrusion 12b, and a tear grip 12c. In one implementation the engaging protrusions engages at one end with the multi-splined shaft 8, at other end with other end it engages with trocar 10 and needle hub 11. This enables transmission of rotational motion and axial motion from multi-splined shaft to the trocar and needle hub assembly. The lockable cylinder can break or allow slipping of the trocar and needle hub assembly with respect to the multi-splined shaft 8 and hence prevents excessive force being transferred to the trocar and needle hub assembly hence preventing any damage. Post insertion, the tear grip 12c is pulled to tear-off to dis-engage the trocar and needle holder assembly from the driver unit by tearing the lockable cylinder.

Figure 8:
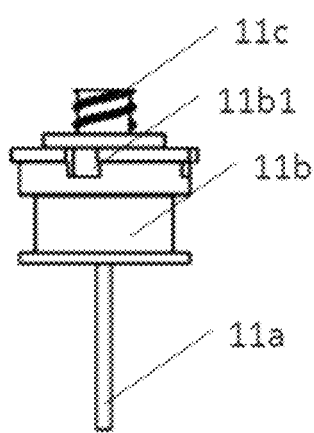
FIG. 8 illustrates a needle hub is shown, in accordance with an embodiment of the present subject matter.

Referring to FIG. 8 illustrate a needle hub is shown, in accordance with an embodiment of the present subject matter. In one implementation, as shown in FIG. 8 the needle hub 11/11b comprises of a needle 11a, a locking surface/groove 11b, and a hub inlet 11c. The operation of working of the needle hub in conjugation with the other components of the device is as explained above.

Figure 9:
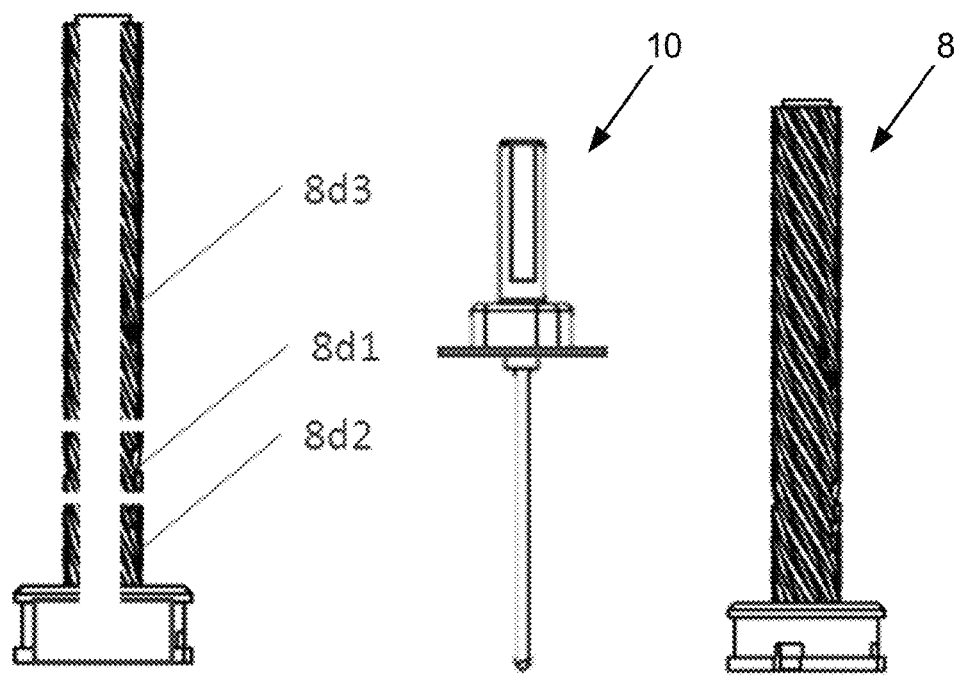
FIG. 9 illustrates a multi segment lead screw is shown, in accordance with an embodiment of the present subject matter.

Referring to FIG. 9 illustrate a multi segment lead screw is shown, in accordance with an embodiment of the present subject matter.

Referring to FIG. 10 illustrates a stiff protrusion: when trocar is not in place, in accordance with an embodiment of the present subject matter.

Figure 11:
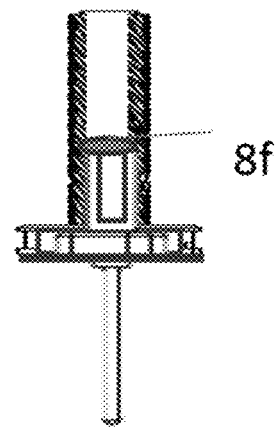
FIG. 11 illustrates a tear able pouch filled with adhesive material is shown, in accordance with an embodiment of the present subject matter.

Referring to FIG. 11 illustrates a tear able pouch filled with adhesive material, in accordance with an embodiment of the present subject matter.

Figure 12:
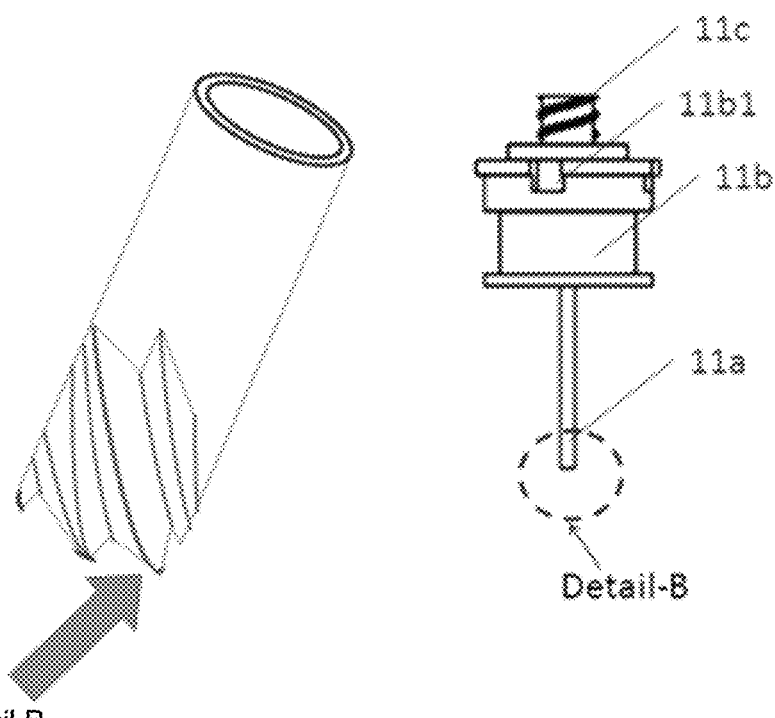
FIG. 12 illustrates an external cutting edge on needle outer surface is shown, in accordance with an embodiment of the present subject matter.

Referring to FIG. 12 illustrates an external cutting edge on needle outer surface, in accordance with an embodiment of the present subject matter. In one implementation, as shown in FIG. 12, the external radial groves on the needle external surface with multiple protrusions are provided so as to facilitate the insertions of the needle into the bone. This may be either in conjunction with trocar with either single point diamond cut or multiple cutting trocar tip will be used in device.

Figure 13:
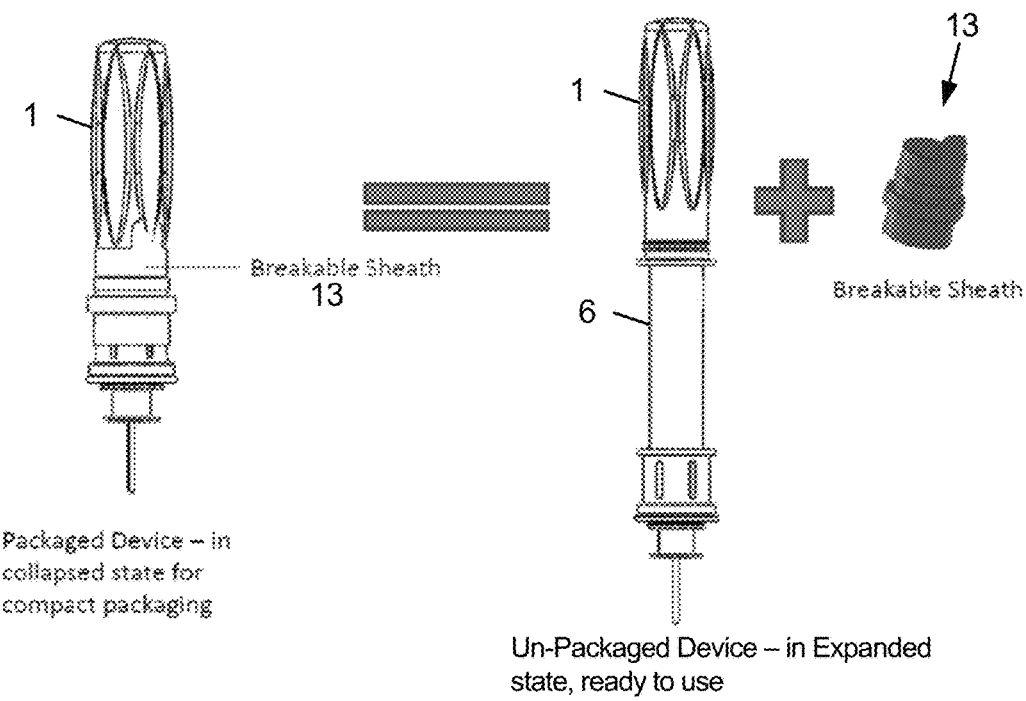
FIG. 13 illustrates a non-reusable 10 device with and without breakable sheath, in accordance with an embodiment of the present subject matter.
Figure 13:
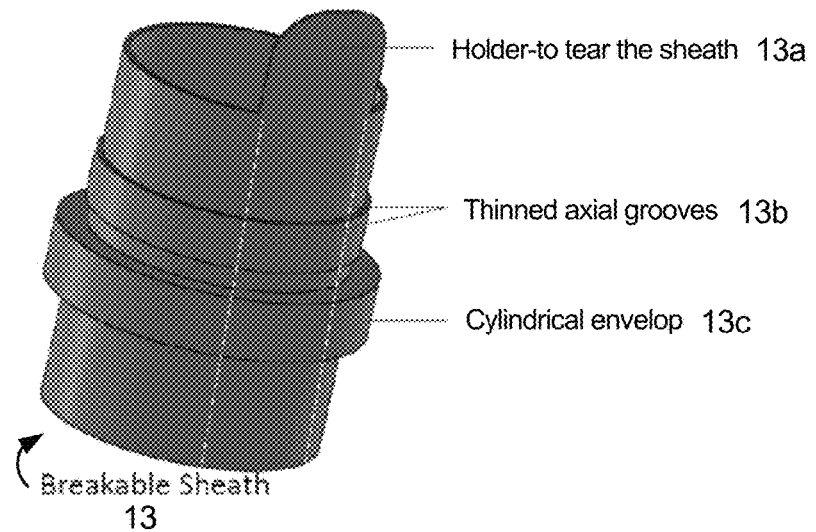

Referring to FIG. 13 illustrates a non-reusable IO device with and without breakable sheath 13, in accordance with an embodiment of the present subject matter.

In one implementation, in assembled condition, the spring loaded device handle is held in collapsed position by breakable sheath 13. The user may have to tear the breakable sheath 13 when handle gets released back. This makes device ready for insertion. In one example, the breakable sheath 13 is cylindrical envelop 13C and thinned axial grooves 13B. When the Holder is pulled axially down, it breaks opens and the handle springs back to un-collapsed position. The breakable sheath 13 may not be re-assembled again and needs to be disposed of.

Figure 14:
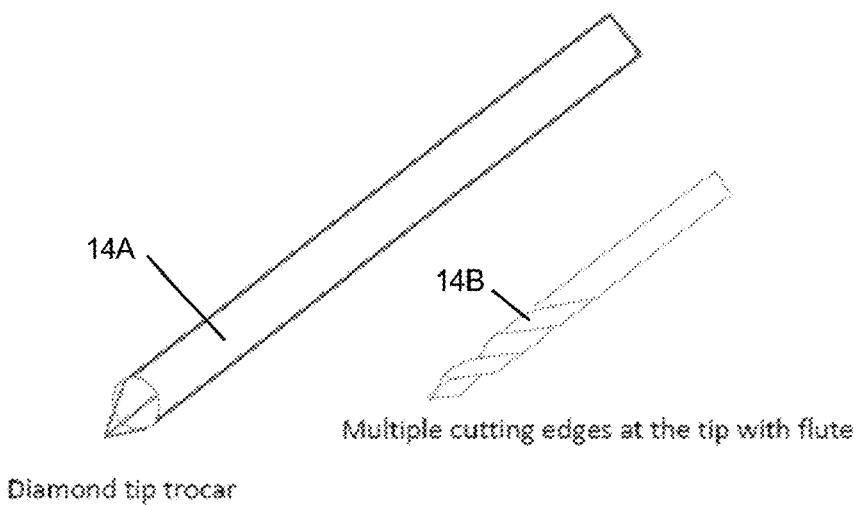
FIG. 14 illustrates a diamond tip trocar tip as used in conventional device, and a multiple cutting edges at the tip with flute tip in accordance with an embodiment of the present subject matter.

Referring to FIG. 14 illustrates a diamond tip trocar tip 14A as used in conventional device, and a multiple cutting edges at the tip with flute tip 14B in accordance with an embodiment of the present subject matter.

Referring to FIGS. 15(a) and (b) illustrates a locking element 9, positioned inside the multi splined shaft 8 and a locking element 9, positioned removed from the multi splined shaft 8, in accordance with an embodiment of the present subject matter.

In one implementation, as shown in FIG. 15(a), the locking element 9 is positioned inside the multi-splined shaft 8. The trocar holder 10, as shown, is assembled into multi splined shaft 8. The expandable element 9a3, as shown, is locked inside hollow cavity 10c of trocar holder shaft 10e.

In one implementation, as shown in FIG. 15(b), when the trocar holder 10 is removed from the multi-splined shaft 8, the expandable element 9a3 is released from the trocar holder shaft 10e and springs back to protrudes out of opening 8a of the multi-spiral shaft 8. The expandable element 9a3 further prevents the axial motion of the multi spiral nut 5. This leads to the locking of the driver unit.

The important features of the present invention are as stated below:

1. The non-reusable intra-osseous access device which can be easily rendered non-reusable after establishing the access into the marrow region includes the automatic locking of driver unit after removal of needle and trocar assembly from the driver unit. The locking of driver unit prevents transmission of rotation and axial motion and/or thrust from the handle to the needle and/or trocar assembly necessary for subsequent insertion.
2. The non-reusable intra-osseous access device which can be easily rendered non-reusable after establishing the access into the marrow region includes the non-loading of the trocar and or needle hub and/or trocar with needle hub necessary for subsequent insertion.
3. The lead screw used in the invention is a multi-segmented screw. In assemble condition, the multi-segmented lead screw acts as a single element and transmits the rotational and axial motion and/or trust necessary for insertion. Upon disengagement of the needle and/or trocar the lead screw gets disintegrated into multiple segments. This leads to non-transmission of prevents transmission of rotation and axial motion and/or thrust from the handle to the needle and/or trocar assembly necessary for subsequent insertion.
4. During the process when needle and trocar are removed, the present device gets locked, and no other/new trocar and/or needle can be reloaded in the device. This feature of the invention makes it non-reusable.
5. The re-usable feature of the invention avoids the risk of contamination and possibility of spreading infection by the re-use of device.
6. For ease of insertion, there are external cutting edges on the needle, which ensures that the cutting remains of the bone/flesh are radially pushed out of the insertion site.
7. If excessive pressure is applied on the handle, the trocar holder and needle hub assembly slips with respect to the multi-splined shaft because of locking cylinder, preventing transmission of excess forces to trocar holder and needle hub leading to prevention of damage to the insertion site.

Accordingly, in one implementation, a non-reusable Intraosseous (IO) device is disclosed. The device comprises of a handle capable of being displaced by applying force, the handle comprising a spring-clutch and an inner barrel; a multi-splined axial shaft capable of being rotated. The multi-splined axial shaft comprising a tear able pouch filled with adhesive material in an axial hollow cavity and at least one opening. The locking mechanism may include at least one expandable element. The trocar holder may include a trocar and a trocar holder shaft. The needle hub may include at least one needle. In one implementation, the trocar holder is inside the multi-splined shaft with a trocar holder shaft inside the axial hollow cavity to block the opening, preventing the expandable element to protrude outside the multi-splined shaft through opening. When the handle is displaced axially down, it compresses the spring-clutch and engages with inner barrel, thereby enabling the multi-spiral nut to move axially down, and rotating the multi-splined shaft, thereafter transferring the rotational motion and axial thrust to the trocar holder and the needle hub, and enabling access through an injection site by rotational piercing action.

In one implementation, a method for using a non-reusable Intraosseous device having a handle capable of being displaced by applying force, the handle comprising a spring-clutch and an inner barrel; multi-splined axial shaft capable of being rotated, the multi-splined axial shaft comprising a tear able pouch filled with adhesive material in a axial hollow cavity and at least one opening; a locking mechanism comprising at least one expandable element, a trocar holder comprising a trocar and a trocar holder shaft; and a needle hub comprising at least one needle is disclosed. The method comprises of: targeting the non-reusable Intraosseous device on the injection site; placing and holding the non-reusable Intraosseous device on the injection site; and applying pressure on the non-reusable Intraosseous device to insert the needle into the injection site thereby establishing access into the injection site. The needle is inserted by a rotational drilling motion.

In one implementation of the present invention, after the method is performed, trocar and needle hub assembly is dismantled from the driver unit post insertion, thereby removing the trocar from the needle hub.

In one implementation of the present invention, the bone marrow is aspirated through the needle hub by engaging the syringe (needle) with needle hub.

In one implementation of the present invention, the fluids are infused through the needle hub into intraosseous space.

In one implementation, the device comprises a spring type lead screw, at least one nut with multiple spirals (multi-spiral nut), a spring seating cap, and other parts, wherein the handle is coupled to the multi-spiral nut through the inner barrel, and the multi-splined axial shaft is engaged with the multi-spiral nut at one end, and the trocar holder and the needle hub at other end.

In one implementation, the spring type lead screw is present between spring seating cap and the inner barrel, wherein the spring is configured to get compressed during downward displacement of the handle and released during upward displacement of the handle.

In one implementation, during assembled condition the expandable element is locked inside a hollow cavity of the trocar holder.

In one implementation, the trocar holder and needle hub are configured to be dismantled thereby leading to prevention of the rotation of the multi-splined shaft and making the device non-reusable, by at least one of: breaking the tear-able pouch causing the liquid adhesive within the tear-able pouch to ooze out of the opening, wherein one end of the tear-able pouch is attached to one end of the trocar holder shaft; or unlocking of the expandable element from the hollow cavity which enables the expandable element to protrude outside the opening and preventing axial up-down motion of the multi-spiral nut along the multi-splined shaft; or any combination thereof.

In one implementation, the multi-splined shaft is multi segmented with at least one independent segment, and multiple segments are held together to form the multi-splined shaft by the trocar holder shaft during assembled condition.

In one implementation, the trocar holder shaft comprises of a section with at least one flat surface so as to restrict relative rotation and axial movement of the multi-splined shaft, hence, during assembled condition, the multi-spiral nut moves up-down along the multi-splined shaft, thereby leads to transfer of rotational motion to the trocar holder and needle hub during insertion in the injection site.

In one implementation, during dismantling, the trocar holder shaft's removal leads to disintegration of the multi-splined shaft into multiple segments, thereby preventing any rotation of one of the segment to the trocar holder and needle hub for subsequent insertion.

In one implementation, the multi-splined shaft at one end comprises of a stiff protrusions configured to prevent the trocar holder to be seated in assemble condition.

In one implementation, the needle comprises of external cutting edges along the spirals of external surface configured to facilitate the insertion through the rotational action of the trocar hub and needle holder.

In one implementation, the spring type lead screw is a multi segment lead screw and configured to become a single unified shaft upon insertion of the trocar shaft in injection site.

In one implementation, when the trocar is removed from the lead screw, the trocar is configured to protrude out making the inlet smaller and thereby prevents trocar with needle to insert back.

In one implementation, the device comprises of a breakable sheath 13 for holding the handle in collapsed position, wherein the breakable sheath 13 comprises of a holder-to tear the sheath 13A, at least one thinned axial grooves 13B, and a cylindrical envelop.

In one implementation, the trocar is a diamond tip trocar 14A with single pointed tip.

In one implementation, the trocar tip comprises of (at least two) cutting edges along the periphery of the drilling tip with flutes to smooth removal of the hard cortical layer by shearing of hard cortical layer radially. This ensures smooth insertion through the bone as compared to axial piercing action or insertion by diamond tip with rotation.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

Although the present disclosure and its advantages have been described in detail, it should be understood that various changes, substitutions and alternations can be made herein without departing from the scope of the disclosure as defined by the following claims.

The invention claimed is:

1. A non-reusable Intraosseous (IO) device comprising:
a handle capable of being displaced by applying force, the handle comprising a spring-clutch and an inner barrel;
a multi-splined axial shaft engaged with a multi-spiral nut and is capable of being rotated, the multi-splined axial shaft comprising an axial hollow cavity and at least one opening;
a needle hub comprising at least one needle; and
when the handle is displaced axially down, it compresses the spring-clutch and engages with the inner barrel, thereby enabling the multi-spiral nut to move axially down, and rotating the multi-splined axial shaft, thereafter transferring the rotational motion and axial thrust to a trocar holder and the needle hub, and enabling access through an injection site by a rotational piercing action;
wherein
an automatic locking mechanism, operating after enabling access through the injection site, comprising:
at least one expandable element, the trocar holder comprising a trocar and a trocar holder shaft, wherein the trocar holder is inside the multi-splined axial shaft with the trocar holder shaft inside an axial hollow cavity and during assembled condition the expandable element is locked inside a hollow cavity of the trocar holder, wherein
the expandable element is configured to protrude outside the opening preventing axial up-down motion of the multi-spiral nut along the multi-splined axial shaft rendering the non-reusable Intraosseous (IO) device non-reusable; and
at least one spring or at least one spring eyelet configured to press the expandable element to protrude outside the opening preventing axial up-down motion of the multi-spiral nut along the multi-splined axial shaft rendering the non-reusable Intraosseous (IO) device non-reusable post insertion.

2. The non-reusable Intraosseous device as claimed in claim 1, wherein the trocar holder and/or the needle hub are configured to be dismantled after enabling access through the injection site.

3. The non-reusable Intraosseous device as claimed in claim 1 comprising a spring type lead screw, a spring seating cap, and other parts, wherein the handle is coupled to the multi-spiral nut through the inner barrel, and the multi-splined axial shaft is engaged with the multi-spiral nut at one end, and the trocar holder, and the needle hub at the other end wherein the trocar holder is configured to snap on the spring type lead screw, wherein
the multi-splined axial shaft is multi segmented with at least one independent segment, and multiple segments are held together to form the multi-splined shaft by the trocar holder shaft during the assembled condition;
the spring type lead screw is present between spring seating cap and the inner barrel, wherein the spring type lead screw is configured to get compressed during downward displacement of the handle and released during upward displacement of the handle;
the multi-splined shaft at one end comprises stiff protrusions configured to prevent the trocar holder from reloading back into a driver unit rendering the device/trocar and needle hub non-reusable preventing reuse; and
the other parts comprise a cylindrical wrap, an engaging protrusion, and a tear grip.

4. The non-reusable Intraosseous device as claimed in claim 1, wherein, the trocar holder shaft comprises a section with at least one flat surface so as to restrict relative rotation and axial movement of the multi-splined axial shaft, hence, during the assembled condition, the multi-spiral nut moves up-down along the multi-splined axial shaft, thereby leading to the transfer of rotational motion to the trocar holder and needle hub during insertion in the injection site.

5. The non-reusable Intraosseous device as claimed in claim 1, wherein, during dismantling, the removal of the trocar holder shaft leads to disintegration of the multi-splined axial shaft into multiple segments, thereby preventing any rotation of one of the segments to the trocar holder and needle hub for subsequent insertion.

6. The non-reusable Intraosseous device as claimed in claim 1, wherein the needle comprises external cutting edges formed as spirals on an external surface configured to facilitate the insertion through the rotational motion of a trocar hub and needle hub.

7. The non-reusable Intraosseous device as claimed in claim 1, comprising a breakable sheath for holding the handle in a collapsed position, wherein the breakable sheath comprises a holder-to tear the sheath, at least one thinned axial groove, and a cylindrical envelop.

8. The non-reusable Intraosseous device as claimed in claim 1, wherein, a needle tip comprises at least two external cutting grooves along an external periphery of the tip with flutes spiraling upward enabling smooth removal of a hard layer at the injection site by shearing of the hard layer radially, so as to ensure smooth insertion into the injection site.

9. The non-reusable Intraosseous device as claimed in claim 1, wherein a trocar tip comprises at least two cutting edges along the periphery of a drilling tip with flutes enabling smooth removal of a hard layer at the injection site by shearing of the hard layer radially, so as to ensure smooth insertion into the injection site.

10. The non-reusable Intraosseous device as claimed in claim 1, wherein when the trocar is removed from a spring type lead screw, the trocar is configured to protrude out making a hub inlet smaller and thereby preventing the trocar with needle from inserting back.

11. A non-reusable Intraosseous (IO) device comprising:
a handle capable of being displaced by applying force, the handle comprising a spring-clutch and an inner barrel;
a multi-splined axial shaft engaged with a multi-spiral nut and capable of being rotated, the multi-splined axial shaft comprising a tearable pouch filled with adhesive material in an axial hollow cavity and at least one opening;
a needle hub comprising at least one needle; and
when the handle is displaced axially down, it compresses the spring-clutch and engages with inner barrel, thereby enabling the multi-spiral nut to move axially down, and rotating the multi-splined axial shaft, thereafter transferring the rotational motion and axial thrust to a trocar holder and the needle hub, and enabling access through an injection site by rotational piercing action;

wherein
an automatic locking mechanism, operating after enabling access through the injection site, wherein the trocar holder and needle hub are configured to be dismantled thereby leading to prevention of the rotation of the multi-splined shaft and making the device non-reusable, by breaking the tearable pouch causing the liquid adhesive within the tearable pouch to ooze out of the opening, wherein one end of the tear-able pouch is attached to one end of the trocar holder shaft.

12. The non-reusable Intraosseous device as claimed in claim 11, wherein the trocar holder and/or the needle hub are configured to be dismantled after enabling access through the injection site.

13. The non-reusable Intraosseous device as claimed in claim 11, wherein, the trocar holder shaft comprises a section with at least one flat surface so as to restrict relative rotation and axial movement of the multi-splined axial shaft, hence, during the assembled condition, the multi-spiral nut moves up-down along the multi-splined axial shaft, which thereby leads to transfer of rotational motion to the trocar holder and needle hub during insertion in the injection site.

14. The non-reusable Intraosseous device as claimed in claim 11, wherein, during dismantling, the removal of the trocar holder shaft leads to disintegration of the multi-splined axial shaft into multiple segments, thereby preventing any rotation of one of the segments to the trocar holder and needle hub for subsequent insertion.

15. The non-reusable Intraosseous device as claimed in claim 11, wherein the needle comprises external cutting edges formed as spirals on an external surface configured to facilitate the insertion through the rotational motion of the trocar holder and needle hub.

16. The non-reusable Intraosseous device as claimed in claim 11, wherein when the trocar is removed from a spring type lead screw, the trocar is configured to protrude out making a hub inlet smaller and thereby preventing the trocar with needle from inserting back rendering the device/trocar and needle hub non-reusable preventing further reuse.

17. The non-reusable Intraosseous device as claimed in claim 11, comprising a breakable sheath for holding the handle in a collapsed position, wherein the breakable sheath comprises a holder-to tear the sheath, at least one thinned axial grove, and a cylindrical envelop.

18. The non-reusable Intraosseous device as claimed in claim 11, wherein, a needle tip comprises at least two external cutting grooves along an external periphery of the tip with flutes spiraling upward enabling smooth removal of a hard layer at the injection site by shearing of the hard layer radially, so as to ensure smooth insertion into the injection site.

19. The non-reusable Intraosseous device as claimed in claim 11, wherein when the trocar is removed from a spring type lead screw, the trocar is configured to protrude out making a hub inlet smaller and thereby preventing the trocar with needle from inserting back.

* * * * *